United States Patent
Sanbuichi et al.

(10) Patent No.: US 10,772,587 B2
(45) Date of Patent: Sep. 15, 2020

(54) RADIATION IRRADIATION DEVICE

(71) Applicant: FUJIFILM Corporation, Tokyo (JP)

(72) Inventors: Masahito Sanbuichi, Kanagawa (JP); Koichi Eguchi, Kanagawa (JP); Takeyasu Kobayashi, Kanagawa (JP); Yusuke Kitagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 178 days.

(21) Appl. No.: 15/959,287

(22) Filed: Apr. 23, 2018

(65) Prior Publication Data

US 2018/0242933 A1 Aug. 30, 2018

Related U.S. Application Data

(63) Continuation of application No. PCT/JP2016/083454, filed on Nov. 11, 2016.

(30) Foreign Application Priority Data

Nov. 26, 2015 (JP) .................................. 2015-230362
Apr. 12, 2016 (JP) .................................. 2016-079428

(51) Int. Cl.
    *A61B 6/00* (2006.01)
(52) U.S. Cl.
    CPC .............. *A61B 6/4405* (2013.01); *A61B 6/00* (2013.01); *A61B 6/40* (2013.01); *A61B 6/4441* (2013.01); *A61B 6/4452* (2013.01)
(58) Field of Classification Search
    CPC ..... A61B 6/547; A61B 6/4441; A61B 6/4476; A61B 6/4405; G21K 5/04
    See application file for complete search history.

(56) References Cited

U.S. PATENT DOCUMENTS

2014/0098942 A1  4/2014 Omura et al.
2014/0098943 A1  4/2014 Omura et al.
(Continued)

FOREIGN PATENT DOCUMENTS

JP  360182832  12/1985
JP  H0471052   6/1992
(Continued)

OTHER PUBLICATIONS

"International Search Report (Form PCT/ISA/210) of PCT/JP2016/083454," dated Jan. 10, 2017, with English translation thereof, pp. 1-5.

(Continued)

*Primary Examiner* — Don K Wong
(74) *Attorney, Agent, or Firm* — JCIPRNET

(57) ABSTRACT

Provided is a radiation irradiation device that can restrict movement of an arm part during device movement without providing a mechanism that becomes a user's obstacle. The radiation irradiation device includes a radiation generation unit that generates radiation; an arm part having one end to which the radiation generation unit is attached; a support member having one end to which the other end of the arm part is connected so as to be rotationally movable; a body part to which the other end of the support member is connected; a leg part that is provided on a bottom surface of the body part and is capable of traveling on a device placement surface; and an arm locking part that restricts the rotational movement of the arm part. The arm locking part is provided inside the arm part.

21 Claims, 9 Drawing Sheets

(56) References Cited

U.S. PATENT DOCUMENTS

| | | | |
|---|---|---|---|
| 2014/0133627 A1* | 5/2014 | Sakuragi | A61B 6/4429 378/62 |
| 2014/0247918 A1 | 9/2014 | Kang et al. | |
| 2014/0291539 A1 | 10/2014 | Omura | |
| 2015/0078529 A1 | 3/2015 | Tsubota et al. | |
| 2015/0270022 A1 | 9/2015 | Omura | |

FOREIGN PATENT DOCUMENTS

| | | |
|---|---|---|
| JP | 2000333940 | 12/2000 |
| JP | 2004073354 | 3/2004 |
| JP | 2014073321 | 4/2014 |
| JP | 2014073322 | 4/2014 |
| JP | 2014110872 | 6/2014 |
| JP | 2014168690 | 9/2014 |
| JP | 2014195590 | 10/2014 |
| JP | 2015083113 | 4/2015 |
| JP | 2015192853 | 11/2015 |

OTHER PUBLICATIONS

"Written Opinion of the International Searching Authority (Form PCT/ISA/237) of PCT/JP2016/083454," dated Jan. 10, 2017, with English translation thereof, pp. 1-8.

"Office Action of Japanese Counterpart Application," dated Sep. 6, 2016, with English translation thereof, pp. 1-8.

* cited by examiner

RADIATION IRRADIATION DEVICE

CROSS-REFERENCE TO RELATED APPLICATIONS

This application is a Continuation of PCT International Application No. PCT/JP2016/083454 filed on Nov. 11, 2016, which claims priority under 35 U.S.C § 119(a) to Japanese Patent Application No. 2015-230362 filed on Nov. 26, 2015 and Japanese Patent Application No. 2016-079428 filed on Apr. 12, 2016. Each of the above application(s) is hereby expressly incorporated by reference, in its entirety, into the present application.

BACKGROUND OF THE INVENTION

1. Field of the Invention

The present invention relates to a radiation irradiation device having an arm part provided with a radiation source.

2. Description of the Related Art

In the related art, portable radiation irradiation devices used in a case where a patient's radiographic image is captured in operating rooms, examination rooms, or patients rooms have been suggested variously (refer to JP2014-73322A, JP2014-110872A, and JP2015-83113A).

The portable radiation irradiation devices basically include a leg part enabled to travel by wheels, a body part that houses a control unit including a battery for driving a radiation source, an electric circuit related to the driving of the radiation source, and the like and is held on the leg part, and an arm part connected to the body part, and are configured by attaching the radiation source to a tip of the arm part.

In a case where such radiation irradiation devices are used, a radiation irradiation device is first moved to the vicinity of a patient's bed. Next, the radiation source is moved to a desired position by extending the arm part, and a radiation detector is moved to a desired position behind a subject. In this state, the subject is irradiated with radiation by driving the radiation source, and a radiographic image of the subject is acquired by detecting the radiation transmitted through the subject using the radiation detector.

Meanwhile, in a case where the radiation irradiation device is moved, a state where the arm part is folded and the radiation source is housed is brought about. In this case, since there is a concern that the device may be damaged in a case where the arm part provided with the heavy radiation source vibrates, it is necessary to restrict movement of the arm part such that the arm part does not move.

Thus, for example, JP2014-73322A suggests a method of providing an outer peripheral surface of the folded arm part and a pillar at a position that faces the outer peripheral surface of the arm part in a case where the arm part is folded with connecting parts respectively and restricting movement of the arm part by connecting these connecting parts to each other.

SUMMARY OF THE INVENTION

However, in a case where a connecting part for locking the arm part is exposed as described in JP2014-73322A, there is a case where the connecting part may hit a user and become an obstacle.

An object of the invention is to provide a radiation irradiation device that can restrict movement of the arm part during device movement, without providing a mechanism that becomes a user's obstacle, in view of the above problems.

A radiation irradiation device of the invention comprises a radiation generation unit that generates radiation; an arm part having one end to which the radiation generation unit is attached; a support member having one end to which the other end of the arm part is connected so as to be rotationally movable; a body part to which the other end of the support member is connected; a leg part that is provided on a bottom surface of the body part and is capable of traveling on a device placement surface; and an arm locking part that restricts the rotational movement of the arm part. The arm locking part is provided inside the arm part.

Here, the expression "the arm locking part is provided inside the arm part" means that all constituent elements of the arm locking part may not be necessarily provided within the arm part and some constituent elements may be provided inside the support member.

Additionally, in the radiation irradiation device of the above invention, an arm unlocking part that releases the restriction by the arm locking part may be provided at the arm part.

Additionally, in the radiation irradiation device of the above invention, the arm unlocking part may be provided closer to the radiation generation unit side than a center in an extension direction of the arm part.

Additionally, in the radiation irradiation device of the above invention, the arm unlocking part may have a movable part that moves in a direction parallel to the extension direction of the arm part, and the restriction by the arm locking part may be released by the movement of the movable part.

Additionally, in the radiation irradiation device of the above invention, the arm unlocking part may release the restriction by the arm locking part depending on the movement of the movable part to the radiation generation unit side.

Additionally, in the radiation irradiation device of the above invention, the arm unlocking part may release the restriction by the arm locking part depending on the movement of the movable part to the support member side.

Additionally, in the radiation irradiation device of the above invention, the movable part may be a plate-shaped member or a tubular member that slides in the extension direction of the arm part.

Additionally, in the radiation irradiation device of the above invention, the arm locking part may restrict the rotational movement of the arm part, using a locking pin, and a locking part to which the locking pin is locked, and the arm unlocking part may release the locking performed by the locking part as the locking pin is moved by the movement of the movable part.

Additionally, in the radiation irradiation device of the above invention, the arm part may move rotationally only around one axis.

Additionally, in the radiation irradiation device of the above invention, the support member may be configured to be rotatable with an axis passing through a center of a connecting portion of the support member to the body part and extending in a vertical direction as a rotational axis.

Additionally, in the radiation irradiation device of the above invention, a support member locking part that restricts the rotation of the support member may be provided.

Additionally, in the radiation irradiation device of the above invention, the support member locking part may restrict the rotation in a case where the support member is located at a center of a rotational angle.

Additionally, in the radiation irradiation device of the above invention, the support member locking part may restrict the rotation of the support member only in a case where the rotational movement of the arm part is restricted using the arm locking part.

Additionally, in the radiation irradiation device of the above invention, the support member locking part may release the restriction of the rotation of the support member in an interlocking manner with the rotational movement of the arm part.

According to the radiation irradiation device of the invention, since the arm locking part that restricts the rotational movement of the arm part is provided inside the arm part, the movement of the arm part during device movement, can be restricted without providing a mechanism that becomes a user's obstacle.

DESCRIPTION OF THE PREFERRED EMBODIMENTS

Figure 1:
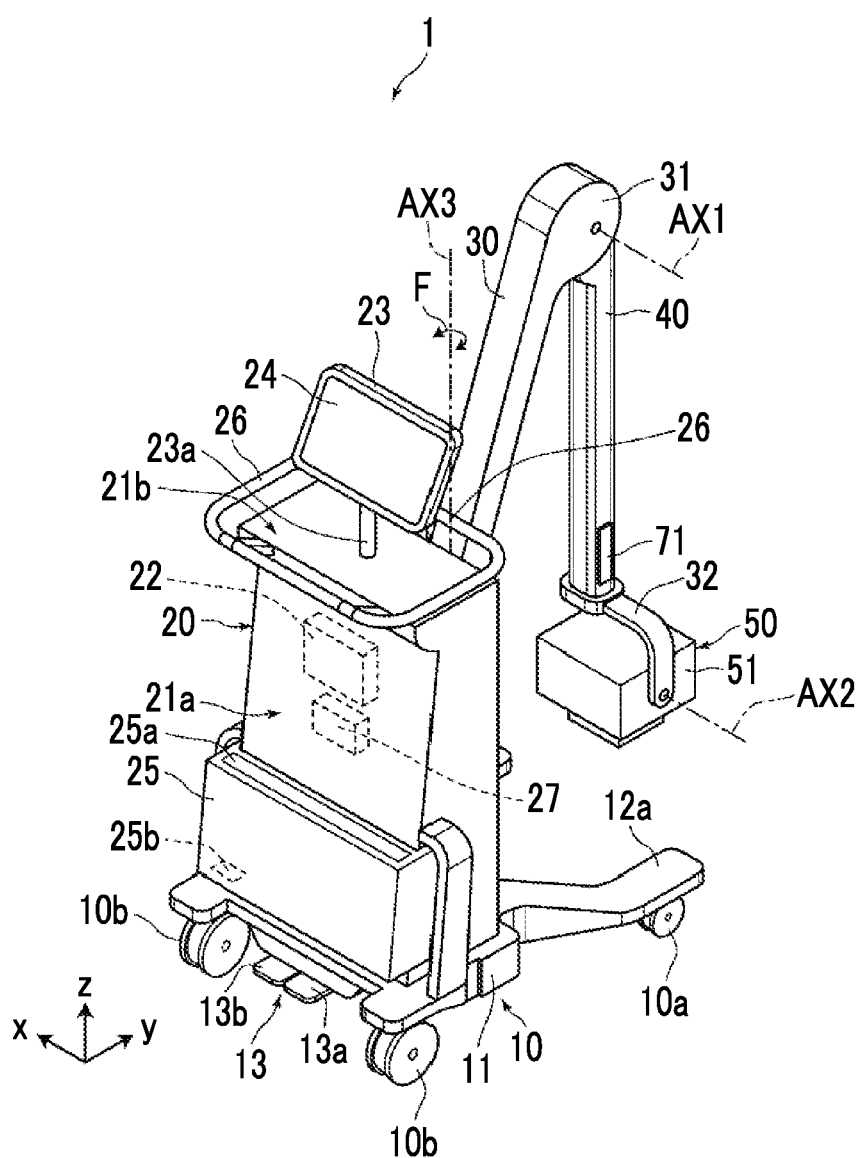
FIG. 1 is a perspective view illustrating an entire shape of a radiation irradiation device of an embodiment of the invention.
Figure 2:
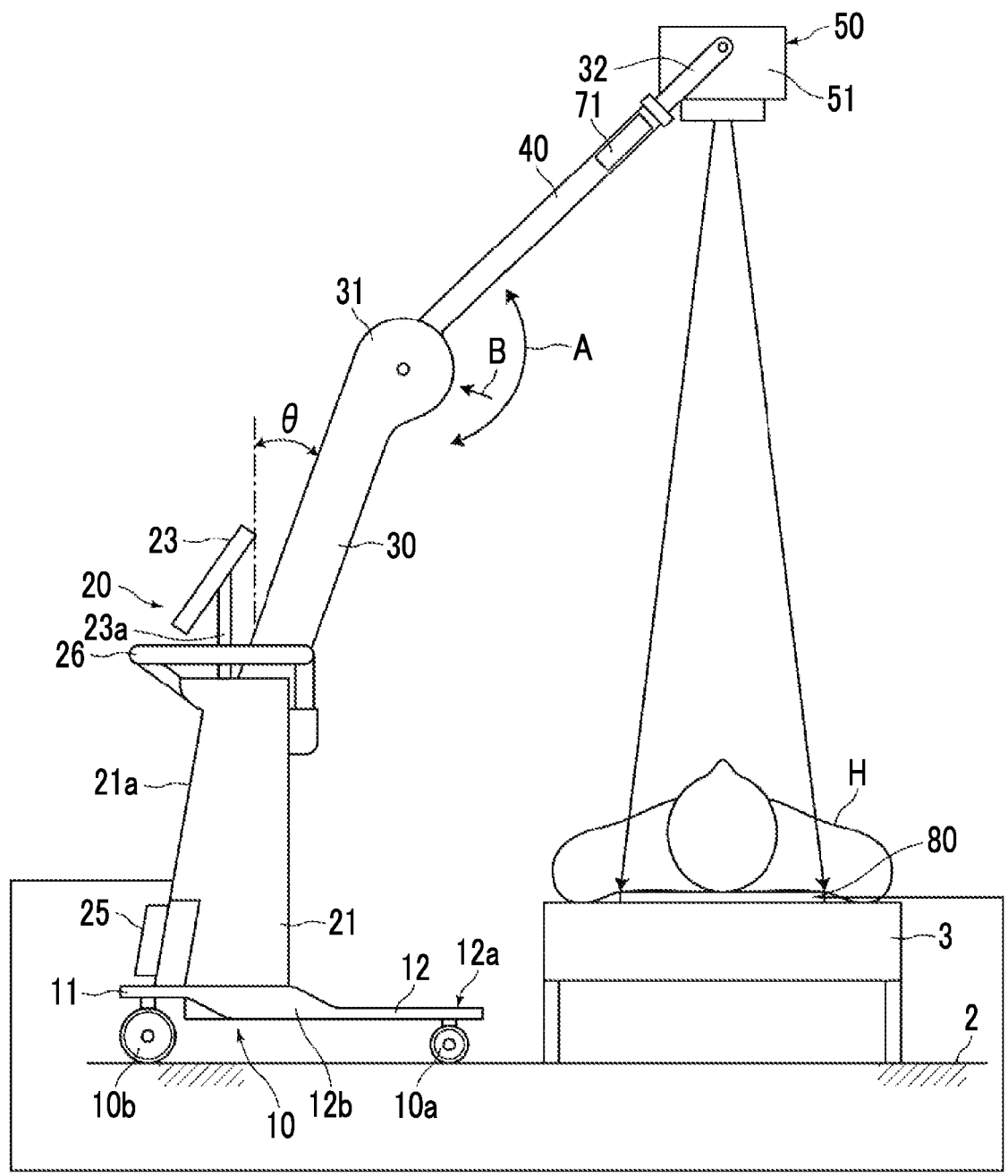
FIG. 2 is a view illustrating the state of the radiation irradiation device of the embodiment of the invention in a case where the device is used.

Hereinafter, a radiation irradiation device of an embodiment of the invention will be described in detail, referring to the drawings. FIG. 1 is a perspective view illustrating the entire shape of the radiation irradiation device of the present embodiment in a case where the device is not used, and FIG. 2 is a side view illustrating the state of the radiation irradiation device of the present embodiment in a case where the device is used. In addition, in the following, an upper side and a lower side in the vertical direction in a state where the radiation irradiation device is placed, for example, a device placement surface, such as a floor of a medical institution, are referred to as "up" and "down", respectively, and a direction perpendicular to the vertical direction in the same state is referred to as a "horizontal" direction. Additionally, in the views to be described below, the vertical direction is defined as a z direction, a right and left direction of the radiation irradiation device is defined as an x direction, and a forward-backward direction of the radiation irradiation device is defined as a y direction. In addition, the front herein means a side toward which an arm part is extended from a body part of the radiation irradiation device in a case where the device is used.

As illustrated in FIGS. 1 and 2, a radiation irradiation device 1 of the present embodiment includes a leg part 10, a body part 20, a support member 30, an arm part 40, and a radiation generation unit 50.

Figure 3:
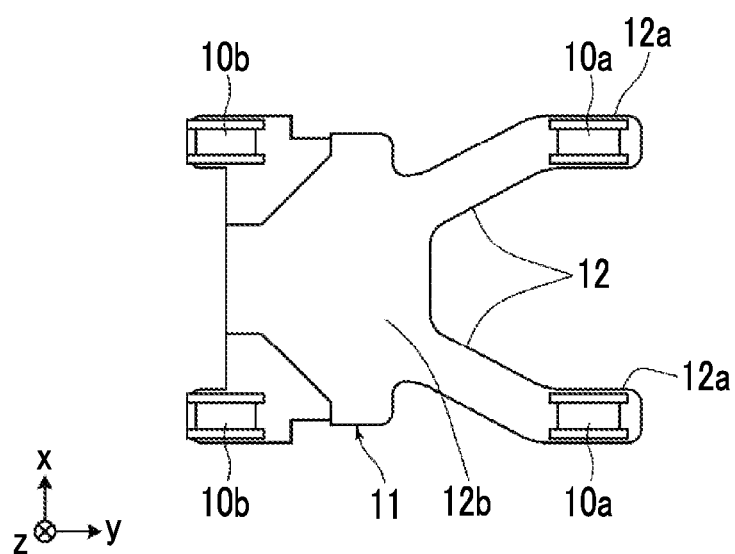
FIG. 3 is a view of a leg part as seen from below.

The leg part 10 is capable of traveling on a device placement surface 2, and includes a plate-shaped pedestal part 11 on which the body part 20 is placed, and a foot arm part 12 that extends from the pedestal part 11 toward the front. FIG. 3 is a view of the leg part 10 as seen from below. As illustrated in FIG. 3, the foot arm part 12 is formed in a V shape that widens in the right and left direction toward the front.

The leg part 10 includes first casters 10a and second casters 10b. The first casters 10a are respectively provided on bottom surfaces of two tip parts 12a at the front of the foot arm part 12, and second casters 10b are respectively provided on bottom surfaces of two corners at the rear of the pedestal part 11. By forming the foot arm part 12 in a V shape as described above, for example, as compared to a case where the entire leg part 10 is formed in a rectangular shape, an edge part of the leg part does not easily collide against its surrounding obstacle in a case where the leg part 10 is rotated. Thus, handling can be made easy. Additionally, weight reduction can also be achieved.

Additionally, as illustrated in FIG. 2, the foot arm part 12 is formed such that the thickness of the two front tip parts 12a in the vertical direction is smaller than the thickness of a V-shaped root part 12b in the vertical direction. In this way, by making the thickness of the two front tip parts 12a of the foot arm part 12 small, it is possible to make the two tip parts 12a easier to enter a location under a bed where a subject is sleeping, or the like, and it is possible to use the device in a narrower space. In addition, the V-shaped root part means a portion where the legs that widen in the right and left direction toward the front join together at the rear side.

Each first caster 10a has a shaft that extends in the upward-downward direction, and is attached to a bottom surface of the foot arm part 12 such that a rotating shaft of a wheel is revolvable within a horizontal plane about the shaft of the first caster. Additionally, each second caster 10b also has a shaft that extends in the upward-downward direction, and is attached to a bottom surface of the pedestal part 11 such that a rotating shaft of a wheel is revolvable within the horizontal plane about the shaft of the second caster. In addition, the rotating shaft of each wheel herein is a rotating shaft in a case where the wheel rotates and travels. The leg part 10 is configured so as to be capable of traveling in a certain direction on the device placement surface 2 by the first casters 10a and the second casters 10b.

Additionally, as illustrated in FIG. 1, a pedal part 13 is provided at the rear of the leg part 10. The pedal part 13 is constituted of two pedals of a first pedal 13a and a second pedal 13b. The first pedal 13a is a pedal for bringing the second casters 10b into a non-revolvable state. As a user steps on the first pedal 13a, the second casters 10b are configured so as to be locked in revolution by a locking mechanism and brought into the non-revolvable state.

Additionally, the second pedal 13b is a pedal for bringing the second casters 10b into a revolvable state from the non-revolvable state. As the user steps on the second pedal 13b, the second casters 10b are configured so as to be released from the locking by the locking mechanism and brought into the revolvable state again.

A well-known configuration can be used as the locking mechanism that locks the revolution of the second casters 10b. For example, the revolution may be locked such that both sides of the wheels of the second casters 10b are sandwiches by plate-shaped members, or the revolution may be locked by providing members that stop the rotation of shafts of the second casters 10b that extend in the upward-downward direction.

The body part 20 is placed on the pedestal part 11 of the leg part 10, and includes a housing 21. A control unit 22 that controls driving of the radiation irradiation device 1 and a charging part 27 are housed within the housing 21.

The control unit 22 performs control regarding generation of radiation and irradiation with radiation, such as a tube current, irradiation time, and a tube voltage, in the radiation generation unit 50, and control regarding acquisition of radiographic images, such as image processing of a radiographic image acquired by a radiation detector to be described below. The control unit 22 is configured of, for example, a computer in which a program for control is installed, exclusive hardware, or a combination of both.

The charging part 27 includes a battery, and charges the radiation detector held by a cradle 25 to be described below. In addition, the charging part 27 is connected to an external power source via a connector (not illustrated), and the battery is charged under the supply of electrical power from the external power source.

Additionally, a monitor 23 is attached to a surface 21b (hereinafter referred to as a monitor installation surface 21b) that faces a bottom surface of the body part 20 via a pillar-shaped connecting member 23a.

The monitor 23 made of a liquid crystal panel or the like, and displays a radiographic image acquired by imaging of the subject, and various kinds of information required for the control of the radiation irradiation device 1. Additionally, the monitor 23 includes a touch panel type input unit 24, and receives input of various instructions required for the operation of the radiation irradiation device 1. Specifically, input for setting of imaging conditions and input for imaging, that is, emission of radiation, is received. In addition, instead of the touch panel type input unit 24, buttons for performing various operations may be included as the input unit.

Figure 4:
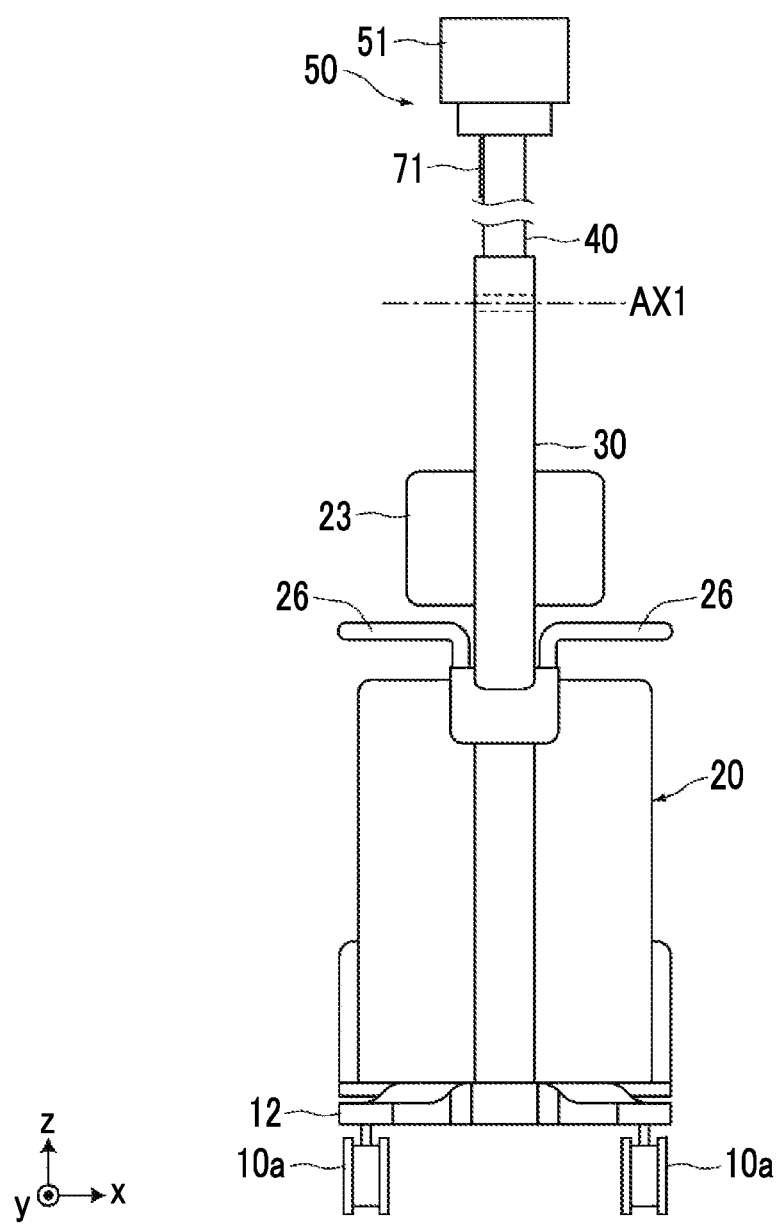
FIG. 4 is a view of the radiation irradiation device illustrated in FIG. 1 as seen from the front.
Figure 5:
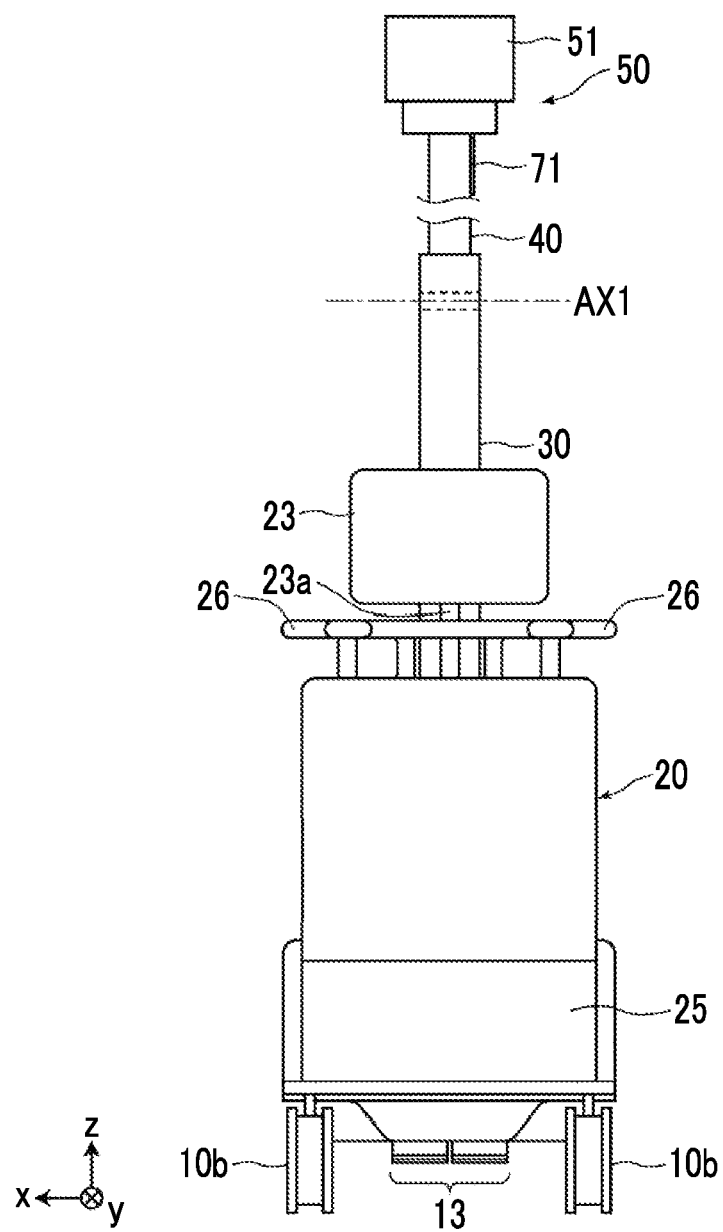
FIG. 5 is a view of the radiation irradiation device illustrated in FIG. 1 as seen from the rear.

Additionally, a body handle part 26 for pushing or pulling the radiation irradiation device 1 is attached to an upper side, in the vertical direction, of the monitor installation surface 21b of the body part 20. The body handle part 26 is provided so as to go around the housing 21, and is configured so as to be capable of being held not only from a rear side of the radiation irradiation device 1 but also from a front side or a lateral side. FIG. 4 is a view of the radiation irradiation device 1 as seen from the front. As illustrated in FIG. 4, the body handle part 26 is provided so as to go around to a front side of the body part 20. FIG. 5 is a view of the radiation irradiation device 1 as seen from the rear.

As illustrated in FIGS. 2 and 5, the connecting member 23a is connected to the monitor installation surface 21b on a lower side in the vertical direction with respect to the body handle part 26, and the monitor 23 is provided such that an end part of the monitor 23 on the lower side in the vertical direction is located on an upper side in the vertical direction with respect to the body handle part 26. By configuring the invention in this way, the user can view the monitor 23 without being disturbed by the body handle part 26, and the visibility of the monitor 23 can be improved.

Additionally, the body part 20 is configured to be capable of housing the radiation detector on the surface thereof opposite to a side where the support member 30 is attached. As the radiation detector, a cassette type radiation detector including a housing is used. Specifically, for example, a radiation detector including a scintillator (fluorescent body) that converts incident radiation into visible light, a photoelectric conversion layer that converts the visible light into electrical signals, and a thin film transistor (TFT) active matrix substrate.

As illustrated in FIGS. 1 and 2, the housing 21 of the body part 20 has a flat surface 21a inclined to the support member 30 side, on a surface opposite to a side where the support member 30 is attached, and the flat surface 21a is provided with the cradle 25.

An insertion port 25a for inserting the radiation detector is formed in an upper surface of the cradle 25. The insertion port 25a has an elongated shape of a size such that the radiation detector is fitted thereto. In the present embodiment, one end part of the radiation detector is inserted into the insertion port 25a, the one end part is supported by the cradle 25, and the radiation detector is held by the cradle 25. In this case, a front surface of the radiation detector is directed to the flat surface 21a side.

A connector 25b is attached to a bottom part of the cradle 25. The connector 25b is electrically connected to the connector of the radiation detector in a case where the radiation detector is held by the cradle 25. The connector 25b is electrically connected to the charging part 27. The charging part 27 charges the radiation detector via the connector 25b. In addition, the charging part 27 is connected to an external power source via a connector (not illustrated), and the battery is charged under the supply of electrical power from the external power source.

The radiation generation unit 50 is configured such that a radiation source, a collimator for narrowing the irradiation range of radiation, and the like is housed within a housing 51. The radiation source is constituted of, for example, an X-ray tube, a booster circuit, and cooling means for cooling the X-ray tube, and the like. Emission of the radiation from the radiation source of the radiation generation unit 50 is performed depending on an instruction from an input unit 24 in the monitor 23 by an operator.

An L-shaped radiation source attachment part 32 is provided at a tip (one end) of the arm part 40. The radiation generation unit 50 is attached to the one end of the arm part 40 via the radiation source attachment part 32. The radiation generation unit 50 is connected to the radiation source attachment part 32 so as to be rotationally movable with an axis AX2 as a rotational movement axis. The rotational movement axis AX2 is an axis that extends in the right and left direction (x direction). In addition, the radiation source attachment part 32 holds the radiation generation unit 50 such that the radiation generation unit 50 moves rotationally via a friction mechanism. For this reason, the radiation generation unit 50 is rotationally movable by applying a certain degree of strong external force, and maintains a relative angle with respect to the arm part 40 without moving rotationally unless an external force is applied.

In addition, the rotational movement of the radiation generation unit 50 may be fixed by a well-known locking mechanism to the rotational movement position.

One end of the support member 30 is connected to the other end of the arm part 40. The arm part 40 is connected to the support member 30 so as to be rotationally movable with an axis AX1 as a rotational movement axis. The rotational movement axis AX1 is an axis that extends in the right and left direction (x direction). The arm part 40 moves rotationally in a direction of arrow A illustrated in FIG. 2 such that an angle formed with the support member 30 is changed about the rotational movement axis AX1. That is, the arm part 40 moves rotationally only around one axis (the rotational movement axis AX1) that extends in the right and left direction. In the present embodiment, as described above, the orientation of the arm part 40 can be freely changed together with the body part 20 by the revolution of the first casters 10a and the second casters 10b. Thus, the degree of freedom of rotation of the arm part 40 can be lowered, and a simpler configuration can be adopted.

A rotational movement part 31 having the rotational movement axis AX1 holds the arm part 40 such that the arm part 40 moves rotationally via the friction mechanism. For this reason, the arm part 40 is rotationally movable by applying a certain degree of strong external force, does not move rotationally unless an external force is not applied, and maintains a relative angle with respect to the support member 30.

Figure 6:
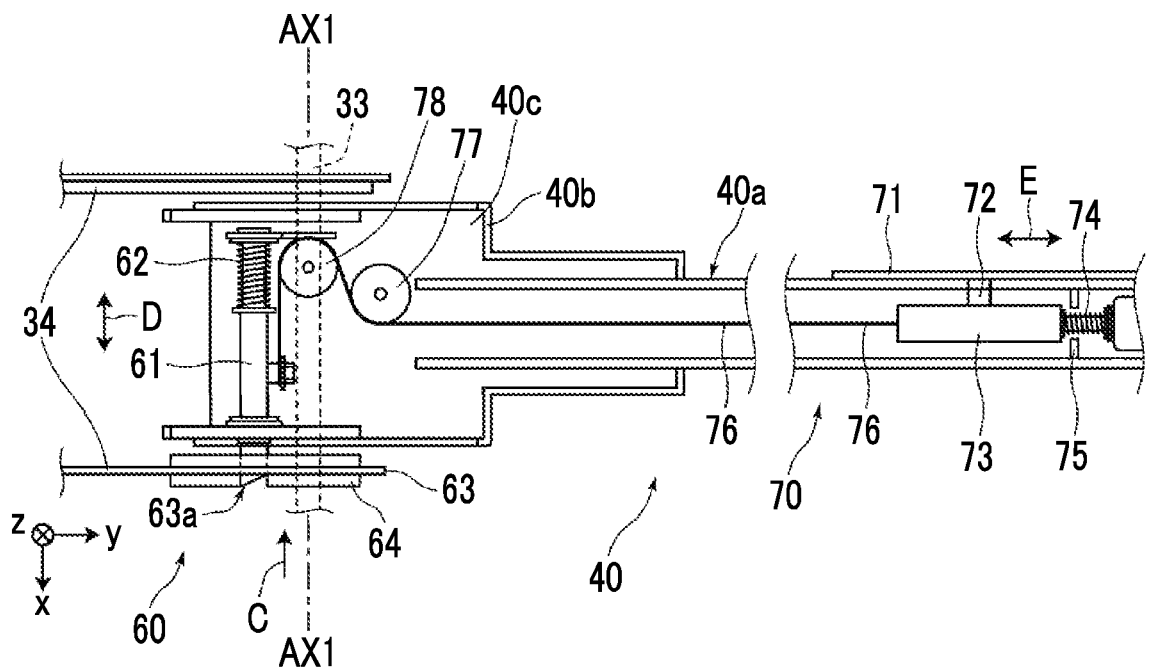
FIG. 6 is a view illustrating the configuration of an arm locking part and an arm unlocking part.
Figure 7:
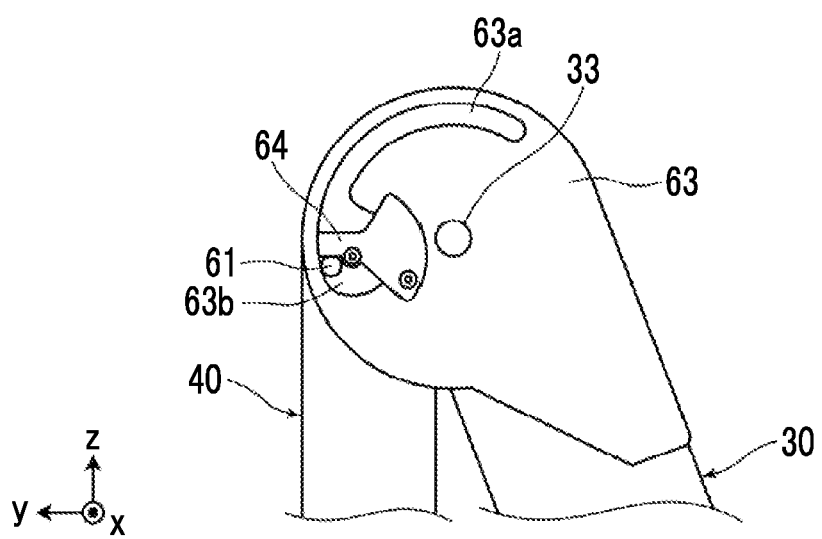
FIG. 7 is a view illustrating the configuration of the arm locking part.

An arm locking part 60 that restricts the rotational movement of the arm part 40 is provided inside the arm part 40 (inside the rotational movement part 31). The arm locking part 60 restricts the rotational movement of the arm part 40 in a case where the arm part 40 is folded and brought into a non-use state, as illustrated in FIG. 1. Hereinafter, the configuration of the arm locking part 60 will be described in detail. FIG. 6 is an internal structure view of the arm part 40 seen from a direction of arrow B in a state where the arm part 40 is extended as illustrated in FIG. 2. Additionally, although FIG. 7 is a view of the arm locking part 60 illustrated in FIG. 6 as seen from a direction of arrow C, and is a view illustrating the state of the arm locking part 60 in a case where being brought into the state where the arm part 40 is folded as illustrated in FIG. 1.

As illustrated in FIG. 6, the arm part 40 includes a tubular arm part body 40a that has the radiation generation unit 50 attached to a tip thereof, and a locking part housing 40b that has the arm part body 40a attached thereto and has a space 40c where the arm locking part 60 is housed.

The arm locking part 60 housed inside the locking part housing 40b includes a locking pin 61 that extends in a direction (x direction) orthogonal to an extension direction of the arm part body 40a, a locking spring part 62 that slides the locking pin 61 in the x direction, and a first plate member 63 and a second plate member 64.

The first plate member 63 and the second plate member 64 are provided at an attachment member 34, and the attachment member 34 is fixed to the support member 30. That is, the first plate member 63 and the second plate member 64 are fixed to the support member 30 via the attachment member 34.

Although the locking pin 61 is biased toward the first and second plate members 63 and 64 side by the locking spring part 62, the locking pin 61 is reciprocated and moved in a direction of arrow D illustrated in FIG. 6 by being pulled by a direction opposite to a direction in which the locking pin 61 is biased by a wire 76 (to be described below) attached to the locking pin 61.

The first plate member 63 is a plate member formed in a teardrop type as illustrated in FIG. 7, and is provided to be fixed to the support member 30 via the attachment member 34 as described above. A first hole 63a and a second hole 63b are formed in the first plate member 63. As illustrated in FIG. 7, a tip of the locking pin 61 is located in the second hole 63b of the first plate member 63 in a state where the arm part 40 is folded, and the tip of the locking pin 61 moves inside the first hole 63a formed in an arc along the arc in a case where the locking pin 61 is shifted from the state where the arm part 40 is folded to a state where the locking pin 61 is extended. In addition, the arm part 40 is extended by rotationally moving around a rotational movement shaft 33 illustrated in FIG. 7. In FIG. 6, although the rotational movement shaft 33 is not illustrated, the rotational movement shaft 33 is disposed at a position illustrated by a dotted line in FIG. 6, and both end parts thereof are fixed to the support member 30.

The second plate member 64 (equivalent to the locking part) is provided on the surface of the first plate member 63. The second plate member 64 is a plate member formed in a fan shape having a protrusion as illustrated in FIG. 7, and is provided to be fixed the surface of the first plate member 63. The first hole 63a and the second hole 63b formed in the first plate member 63 are divided by the protrusion of the second plate member 64. Thus, as the tip of the locking pin 61 inserted into the second hole 63b abuts against and is locked to the protrusion of the second plate member 64, the movement of the locking pin 61 is restricted and thereby the movement of the arm part 40 is restricted. That is, the position of the arm part 40 is fixed in a state where the arm part 40 is folded as illustrated in FIG. 1.

In a case where the arm part 40 is unlocked in a case where the device is used, the locking pin 61 moves in the direction opposite to the biasing direction of the locking spring part 62 by being pulled by the wire 76 as described above, the second plate member 64 is unlocked by the tip of the locking pin 61 slipping out of the second hole 63b, and thereby, the arm part 40 is unlocked. The tip of the locking pin 61 is inserted into the first hole 63a, and the tip of the locking pin 61 moves within the first hole 63a together with the movement of the arm part 40.

Next, the arm unlocking part 70 including the above-described wire 76 will be described. The arm unlocking part 70 includes a movable part 71 that moves in a direction parallel to the extension direction of the arm part 40, a wire connecting member 73 that is connected to the movable part 71 via a pillar part 72 and has the wire 76 connected thereto, a releasing spring part 74 that biases the wire connecting member 73 toward the arm locking part 60 side, a fixing member 75 that fixes the releasing spring part 74, the wire 76 having one end connected to the wire connecting member 73 and the other end connected to the locking pin 61, and two pulleys 77 and 78.

Figure 8:
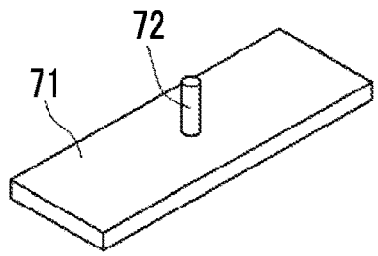
FIG. 8 is a view illustrating an example of a movable part.
Figure 9:
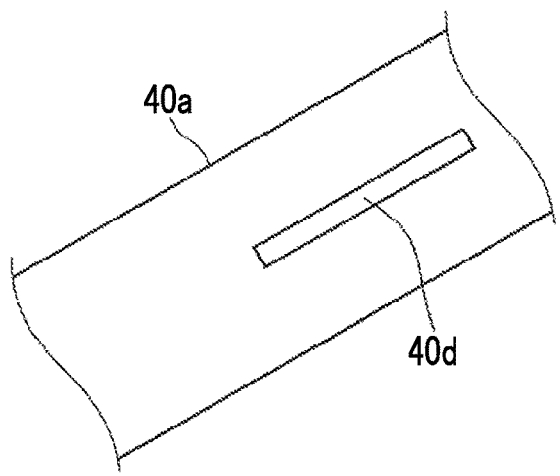
FIG. 9 is a view illustrating an example of a hole provided in the arm part.

As illustrated in FIG. 8, the movable part 71 is a plate-shaped member, and the pillar part 72 connected to the above-described wire connecting member 73 is formed on the surface of the plate-shaped member. As illustrated in FIG. 9, a hole 40d that extends in the extension direction of the arm part body 40a is formed in the arm part body 40a. Thus, the pillar part 72 of the movable part 71 is inserted into the hole 40d, and the movable part 71 is installed on an outer surface of the arm part body 40a. The pillar part 72 inserted into the hole 40d of the arm part body 40a is connected to the wire connecting member 73 installed within the arm part body 40a, and thereby, the movable part 71 and the wire connecting member 73 are connected together with a wall part of the arm part body 40a sandwiched therebetween.

In addition, in the present embodiment, the movable part 71 is formed in a flat plate shape. However, the invention is not limited to this, and the movable part 71 may be formed in a tubular shape. The shape of the movable part 71 may be combined with the shape of the arm part body 40a. For example, in a case where the arm part body 40a is formed in a cylindrical shape, a cross-section of the movable part 71 may be formed in a circular-arc plate shape or may be formed in a cylindrical shape. In a case where the movable part 71 is formed in a tubular shape, it is more preferable because the movable part 71 is easily held in a case where the user moves the movable part 71.

The movable part 71 moves in the extension direction of the arm part 40 along an outer surface of the arm part 40 as the user applies an external force. The wire connecting member 73 moves in the extension direction of the arm part 40 by the movement of the movable part 71. The wire connecting member 73 is configured to move in the same direction as the user holds the movable part 71 to move the movable part 71 toward the radiation generation unit 50 side, and to return in the opposite direction (toward the arm locking part 60 side) by the biasing of the releasing spring part 74 as the user lifts his/her hand from the movable part 71. That is, the wire connecting member 73 is configured so as to reciprocally move in a direction of arrow E illustrated in FIG. 6.

In a case where the wire connecting member 73 has moved toward the radiation generation unit 50 side, the wire 76 with having one end connected to the wire connecting member 73 is pulled toward the radiation generation unit 50 side together with this movement. The other end of the wire 76 is connected to the locking pin 61 such that an extension direction thereof is changed to a direction parallel to the locking pin 61 by the two pulleys 77 and 78. In a case where the wire 76 is pulled toward the radiation generation unit 50 side as described above, the locking pin 61 is pulled by the wire 76 and moves toward a side opposite to the first and second plate members 63 and 64 side, and the locking pin 61 is unlocked.

In a case where the movable part 71 and the wire connecting member 73 has moved toward the side opposite to the radiation generation unit 50 side as the user lifts his/her hand from the movable part 71, the locking pin 61 moves toward the first and second plate members 63 and 64 side by the biasing of the locking spring part 62. In a case where the tip of the locking pin 61 is inserted into the first hole 63a as described above, the arm part 40 is unlocked and the extension of the arm part 40 is allowed.

In addition, it is desirable that a tip part of the locking pin 61 on the first and second plate members 63 and 64 side are formed in a tapered shape, or as illustrated in FIG. 6, an end surface is an inclined surface having a gradient that is not perpendicular to a side surface of the locking pin 61. By configuring the invention in this way, in a case where the arm part 40 is shifted from a movable state to a locked state, that is, in a case where the tip part of the locking pin 61 is moved from the first hole 63a of the first plate member 63 to the second hole 63b thereof, the inclined surface of the tip part of the locking pin 61 can be moved while sliding on the protrusion of the second plate member 64. Thus, the locking pin 61 can be moved toward the locking spring part 62 side without the user moving the movable part 71 in an unlocking direction (radiation generation unit 50 side). That is, the arm part 40 can be automatically brought into the locked state simply by the user folding the arm part 40 in the non-use state. In addition, in a case where the inclined surface having a gradient is formed at the tip part of the locking pin 61, the inclined surface and the protrusion of the second plate member 64 are configured so as to face each other and are in contact with each other.

It is preferable that the movable part 71 is provided closer to the radiation generation unit 50 side than the center of the arm part 40 in the extension direction, and it is more preferable to provide the movable part 71 is provided at an end part of the arm part body 40a in the vicinity of the radiation generation unit 50. By providing the movable part 71 at such a position, the unlocking operation of the arm part 40 by the user and the operation of extending the arm part 40 can be performed through the series of operations without moving the user's hand.

Additionally, in the present embodiment, the arm part 40 is unlocked by moving the movable part 71 toward the radiation generation unit 50 side. However, contrary to this, the arm part 40 may be unlocked by moving the movable part 71 toward the support member 30 side (arm locking part 60 side). In this case, the unlocking direction may be changed to the support member 30 side by adding one pulley into the locking part housing 40b and folding back the orientation of the wire 76. In this way, since the user draws the movable part 71 close to the user side at the time of unlocking by changing the unlocking direction to the support member 30 side, it becomes easier to operate the device.

The above is the description of the arm locking part 60 and the arm unlocking part 70. In addition, the constituent elements of the arm locking part 60 and the arm unlocking part 70 are not limited to the above-described ones, and these constituent elements may be configured using a combination of a belt, a gear and a rack, a pinion, and the like as long as a mechanism that moves the locking pin 61 is provided similarly to the above.

In addition, in the present embodiment, the arm part 40 does not have an extendable and retractable configuration, and is configured to be incapable of being extended and retracted. In the present embodiment, as described above, the orientation of the arm part 40 can be freely changed together with the body part 20 by the revolution of the first casters 10a and the second casters 10b. Thus, it is not necessary to provide a configuration in which the arm part 40 is extended and retracted, and a simpler configuration can be adopted. However, the invention is not limited to such a configuration and a configuration in which the arm part 40 is extendable and retractable may be adopted.

The other end of the support member 30 is connected to the surface of the body part 20 on the front side. The support member 30 is configured to be rotatable with respect to the body part 20. Specifically, as illustrated in FIG. 1, the support member 30 may be configured so as to be rotatable in a direction of arrow F, with an axis passing through the center of the connecting portion of the support member 30 to the body part 20 and extending in the vertical direction (z direction) as a rotational axis AX3.

Figure 10:
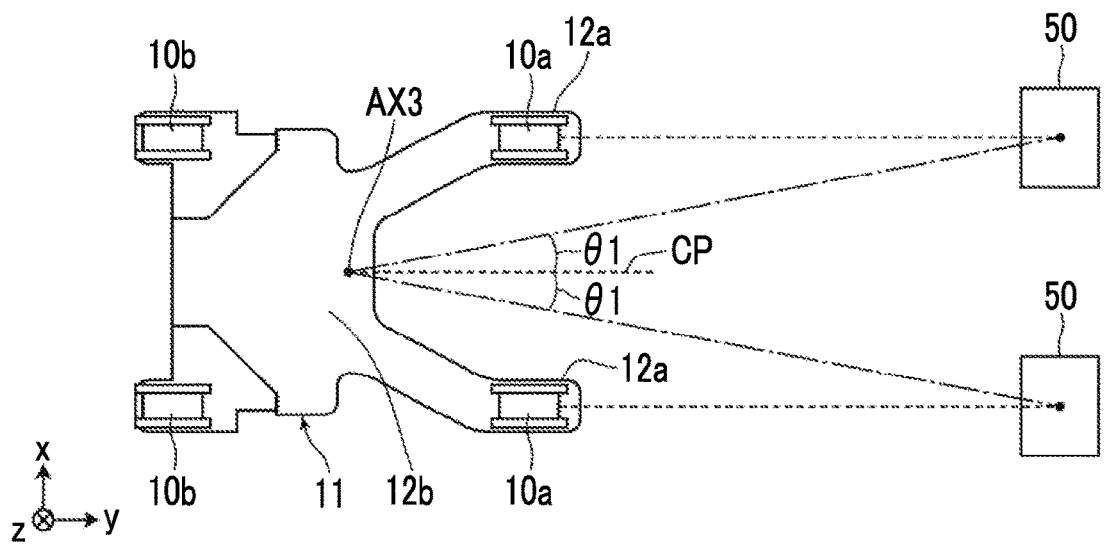
FIG. 10 is a view illustrating an example of a maximum rotational angle of a support member.

FIG. 10 is a view illustrating an example of a maximum rotational angle of the support member 30, and is a view of the radiation irradiation device 1 as seen from the bottom. As illustrated in FIG. 10, it is desirable that a maximum rotational angle θ1 of the support member 30 is an angle at which the position, in the right and left direction (x direction), of the radiation generation unit 50 in a case where the arm part 40 is extended to the maximum toward the front becomes the same position as the positions of the front first casters 10a in the right and left direction (x direction). By setting the maximum rotational angle θ1 in this way, the weight balance of the entire device can be prevented from collapsing in a case where the arm part 40 is extended. Additionally, since the support member 30 is not vainly rotated in a case where the radiation generation unit 50 is moved to a position immediately above a predetermined position of the subject on a bed, alignment of the irradiation position with respect to the subject can be performed easily.

Figure 11:
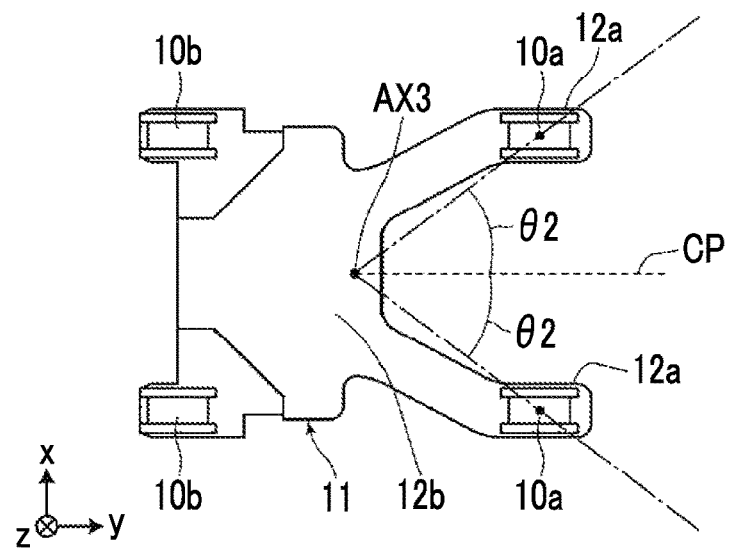
FIG. 11 is a view illustrating another example of the maximum rotational angle of the support member.

Additionally, the maximum rotational angle of the support member 30 is not limited to the angle illustrated in FIG. 10. For example, the support member 30 may be configured to be rotatable up to an angle illustrated in FIG. 11. That is, an angle at which an axis extending in the length direction of the support member 30 and the arm part 40 comes to a position on a straight line connecting the rotational axis AX3 of the support member 30 and the centers of the front first casters 10a to each other may be a maximum rotational angle θ2.

The maximum rotational angle of the support member 30 is preferably ±20° and more preferably 15° more preferably with respect to a central position CP of the maximum rotational angle.

Additionally, in the present embodiment, the support member 30 is configured such that the rotation thereof is locked at the central position CP of the maximum rotational angle. By locking the rotation of the support member 30 at the central position CP of the maximum rotational angle in this way, the support member 30 and the arm part 40 can be disposed at a central position of the radiation irradiation device 1 in the right and left direction, for example, in a case where the radiation irradiation device 1 is moved, weight balance can be maintained and straightness can be improved. Additionally, the arm part 40 can be prevented from colliding against surrounding things.

Figure 13:
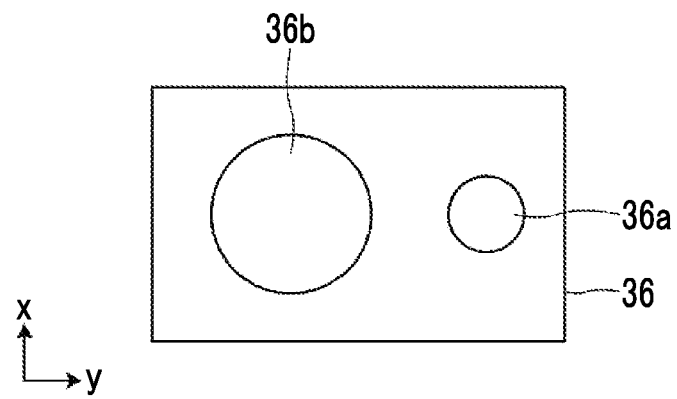
FIG. 13 is a top view of a rotation restricting plate.
Figure 14:
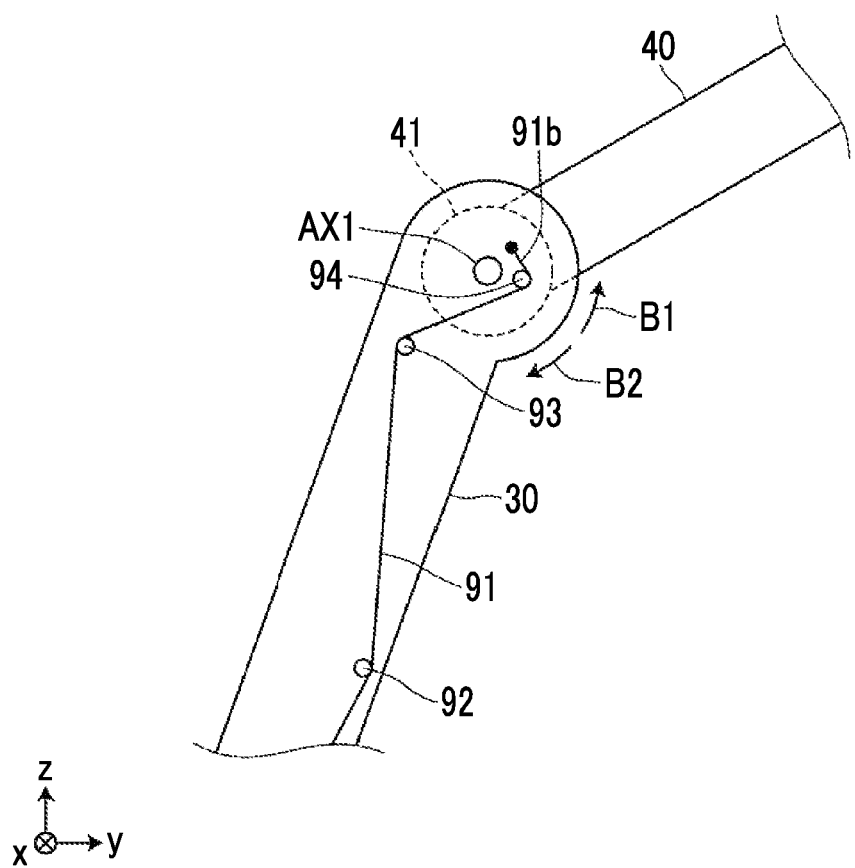
FIG. 14 is a view illustrating a schematic configuration of the support member locking part.

Hereinafter, a support member locking part 90 that locks the rotation of the support member 30 will be described in detail, referring to FIGS. 12 to 14.

First, a rotating mechanism 35 is provided at the connecting portion of the support member 30 to the body part 20. The support member 30 is configured to be rotatable up to the above-described maximum rotational angle with the rotational axis AX3 as a center by the rotating mechanism 35. The rotating mechanism 35 holds a support member body 30a such that the support member body 30a rotates via a friction mechanism. Hence, the support member 30 including the support member body 30a is rotatable by a certain degree of strong external force being applied thereto, and maintains a relative angle with respect to the body part 20 with being rotated unless an external force is applied.

The above-described support member locking part 90 is further provided. Thus, in a case where the rotation is locked by the support member locking part 90, the support member 30 is configured so as not to rotate even in a case where an external force is applied.

The support member locking part 90 includes a rotation restricting plate 36 and a locking shaft 37. FIG. 13 is a top view of the rotation restricting plate 36. As illustrated in FIG. 13, the rotation restricting plate 36 is provided with a first opening 36a and a second opening 36b. The above-described rotating mechanism 35 is provided within the second opening 36b of the rotation restricting plate 36. As one end 37a of the locking shaft 37 provided within the support member 30 is inserted into the first opening 36a of the rotation restricting plate 36, and the one end 37a of the locking shaft 37 is engaged with an inner wall of the first opening 36a, the rotation of the support member 30 is locked. The first opening 36a of the rotation restricting plate 36 is formed at a position locked in a case where the support member 30 is located at the central position CP (refer to FIGS. 10 and 11) of the maximum rotational angle as described above.

Figure 12:
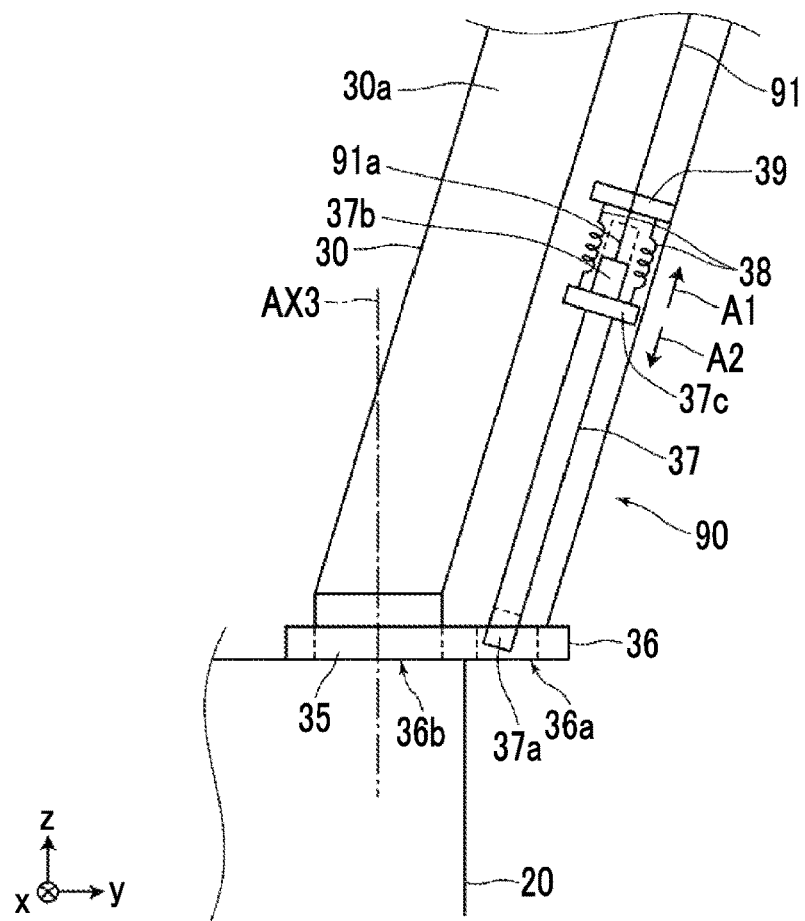
FIG. 12 is a view illustrating a schematic configuration of a support member locking part.

The locking shaft 37 is configured to be movable in a direction of arrow A1 and in a direction of arrow A2 that are illustrated in FIG. 12. In a case where the locking shaft 37 has moved up to a position illustrated by a dotted line of FIG. 12, and thereby, the one end 37a of the locking shaft 37 has slipped out of the first opening 36a, the support member 30 is unlocked. Specifically, the support member locking part 90 includes a wire 91, and one end 91a of the wire 91 is connected to the other end 37b of the locking shaft 37. By pulling the wire 91 in the direction of arrow A1, the locking shaft 37 moves in the direction of arrow A1, and the one end 37a of the locking shaft 37 slips out of the first opening 36a of the rotation restricting plate 36.

Moreover, the support member locking part 90 includes two spring members 38. One end of each of the two spring members 38 is connected to a fixing member 39 fixed to a housing of the support member 30, or the like, and the other end of each of the two spring members 38 is connected to a flange 37c provided to be fixed to the locking shaft 37. The two spring members 38 biases the locking shaft 37 in the arrow A2 direction (toward the rotation restricting plate 36 side), and move the locking shaft 37 in the direction of arrow A2 in a case where the tension of the locking shaft 37 in the direction of arrow A1 by the wire 91 is loosened.

The support member locking part 90 restricts the rotation of the support member 30 only in a case where the rotational movement of the arm part 40 is locked by the above-described arm locking part 60. Specifically, as illustrated in FIG. 14, the other end 91b of the wire 91 is connected to a rotating plate 41 via three pulleys 92, 93, and 94. The rotating plate 41 is connected to the arm part 40, and rotates with the rotational movement axis AX1 as an axis together with the rotational movement of the arm part 40.

Hence, as the rotating plate 41 rotates in a direction of arrow B1, the wire 91 is pulled in the direction of arrow A1 illustrated in FIG. 12, and as the rotating plate 41 rotates in a direction of arrow B2, the tension of the wire 91 in the direction of arrow A1 is loosened.

As illustrated in FIGS. 1 and 7, the wire 91 is set to have such a length that the one end 37a of the locking shaft 37 is inserted into the first opening 36a of the rotation restricting plate 36, in a state where the arm part 40 is folded (that is, in a state where the rotational movement of the arm part 40 is locked), and is set to have such a length that the one end 37a of the locking shaft 37 slips out of the first opening 36a of the rotation restricting plate 36, in a case where the arm part 40 is unlocked and the arm part 40 moves rotationally. Accordingly, the rotation of the support member 30 can be restricted only in a case where the rotational movement of the arm part 40 is locked by the arm locking part 60 as described above. By configuring the invention in this way, the rotation of the support member 30 can be unlocked in an interlocking manner with the rotational movement of the arm part 40, and the operability of the device can be improved.

In addition, in above description, the rotation of the support member 30 is unlocked in an interlocking with the rotational movement of the arm part 40 by connecting the other end 91b of the wire 91 of the support member locking part 90 to the rotating plate 41. However, the invention is not limited to this, and the other end 91b of the wire 91 may be connected to the wire 76 of the arm unlocking part 70. As a result, in a case where the user moves the movable part 71 of the arm unlocking part 70, the wire 91 of the support member locking part 90 is pulled together with the wire 76 of the arm unlocking part 70, and both the rotational movement of the arm part 40 and the rotation of the support member 30 can be unlocked. That is, the unlocking of the rotational movement of the arm part 40 and the unlocking of the rotation of the support member 30 can be interlocked with each other.

In addition, in the above description, in a case where the rotational movement of the arm part 40 is locked, the rotation of the support member 30 is locked as the one end 37a of the locking shaft 37 is inserted into the first opening 36a of the rotation restricting plate 36. However, the method of locking the rotation of the support member 30 is not limited to this. For example, in a case where the rotating mechanism 35 of the support member 30 is provided with a friction brake mechanism having rubber or the like and the rotational movement of the arm part 40 is locked, the rotation of the support member 30 may be locked by the friction brake mechanism.

Additionally, in the above description, the first opening 36a is provided on the rotation restricting plate 36 side and the locking shaft 37 is fitted to the first opening. However, the arrangement may be reversed, that is, a protrusion may be provided on the rotation restricting plate 36 side, and a member having a recess fitted to the protrusion may be provided on the locking shaft 37 side. The above is description regarding the support member locking part 90.

Additionally, in the present embodiment, the support member 30 is configured to be rotatable with respect to the body part 20. However, the invention is not limited to this, and the support member 30 may be provided to be fixed to the body part 20, and may be configured to be non-rotatable. In this case, a simpler configuration can be adopted.

Additionally, as illustrated in FIG. 2, the support member 30 of the present embodiment is provided such that the inclination θ of the extension direction thereof with respect to the vertical direction become 30 degrees or more and 10 degrees or less. By setting the inclination θ of the support member 30 to 10 degrees or more, the user's front visibility can be secured. Additionally, by setting the inclination θ of the support member 30 to 30 degrees or less, the arm part 40 can be folded downward and the radiation generation unit 50 can be housed. Additionally, in a case where the radiation irradiation device 1 is used, a source image receptor distance (SID) can be secured.

In addition, the extension direction of the support member 30 means an axial direction thereof in a case where the support member 30 is formed linearly. Additionally, the extension direction means a direction in which a straight line connecting the centers of both end parts of the support member 30 together extends in a case where the support member 30 is formed in shapes, such as an arc, other than the straight line.

In the present embodiment, in a case where the subject is imaged, as illustrated in FIG. 2, the radiation detector 80 is disposed under the subject H that lies on ones' back on a bed 3. As the user rotationally moves the arm part 40 around the rotational movement axis AX1 in an illustrated counter-clockwise direction from an initial position of the arm part 40 illustrated in FIG. 1, the radiation generation unit 50 is moved to a target position immediately above the subject H, as illustrated in FIG. 2.

The radiographic image of the subject H can be acquired by driving the radiation generation unit 50 according to an instruction from the input unit 24 to irradiate the subject H with radiation and detecting the radiation transmitted through the subject H, using the radiation detector 80, after the radiation generation unit 50 is moved to the target position. In addition, the radiation detector 80 and the radiation irradiation device 1 are connected together with or without wires. Accordingly, the radiographic image of the subject H acquired by the radiation detector 80 is directly input to the radiation irradiation device 1.

EXPLANATION OF REFERENCES

1: radiation irradiation device
3: bed
10: leg part
10a: first caster
10b: second caster
11: pedestal part
12: foot arm part
13: pedal part
20: body part
21: housing
22: control unit
23: monitor
24: input unit
25: cradle
26: body handle part
27: charging part
30: support member
30a: support member body
31: rotational movement part
32: radiation source attachment part
33: rotational movement shaft
34: attachment member
35: rotating mechanism
36: rotation restricting plate
36a: first opening
36b: second opening
37: locking shaft
37a: one end of locking shaft
37b: other end of locking shaft
37c: flange
38: spring member
39: fixing member
40: arm part
40a: arm part body
40b: locking part housing
40c: space
40d: hole
41: rotating plate
50: radiation generation unit
51: housing
60: arm locking part
61: locking pin
62: locking spring part
63: first plate member
63a: first hole
63b: second hole
64: second plate member
70: unlocking part
71: movable part
72: pillar part
73: wire connecting member
74: releasing spring part
75: fixing member
76: wire
77, 78: pulley
80: radiation detector
90: support member locking part
91: wire
91a: one end of wire
91b: other end of wire
92 to 94: pulley
AX1, AX2: rotational movement axis AX3: rotational axis
CP: central position of maximum rotational angle
θ1, θ2: maximum rotational angle

What is claimed is:

1. A radiation irradiation device comprising:
a radiation generation unit that generates radiation;
an arm part having one end to which the radiation generation unit is attached;
a support member having one end to which the other end of the arm part is connected so as to be rotationally movable;
a body part to which the other end of the support member is connected;
a leg part that is provided on a bottom surface of the body part and is capable of traveling on a device placement surface; and
an arm locking part that restricts the rotational movement of the arm part,
wherein the arm locking part is provided inside the arm part and attached to the support member.

2. The radiation irradiation device according to claim 1, wherein an arm unlocking part that releases the restriction by the arm locking part is provided at the arm part.

3. The radiation irradiation device according to claim 2, wherein the arm unlocking part is provided closer to the radiation generation unit side than a center of the arm part in an extension direction of the arm part.

4. The radiation irradiation device according to claim 2, wherein the arm unlocking part has a movable part that moves in a direction parallel to an extension direction of the arm part, and
wherein the restriction by the arm locking part is released by the movement of the movable part.

5. The radiation irradiation device according to claim 3, wherein the arm unlocking part has a movable part that moves in a direction parallel to the extension direction of the arm part, and
wherein the restriction by the arm locking part is released by the movement of the movable part.

6. The radiation irradiation device according to claim 4, wherein the arm unlocking part releases the restriction by the arm locking part depending on the movement of the movable part to the radiation generation unit side.

7. The radiation irradiation device according to claim 5, wherein the arm unlocking part releases the restriction by the arm locking part depending on the movement of the movable part to the radiation generation unit side.

8. The radiation irradiation device according to claim 4, wherein the arm unlocking part releases the restriction by the arm locking part depending on the movement of the movable part to the support member side.

9. The radiation irradiation device according to claim 5, wherein the arm unlocking part releases the restriction by the arm locking part depending on the movement of the movable part to the support member side.

10. The radiation irradiation device according to claim 4, wherein the movable part is a plate-shaped member or a tubular member that slides in the extension direction of the arm part.

11. The radiation irradiation device according to claim 5, wherein the movable part is a plate-shaped member or a tubular member that slides in the extension direction of the arm part.

12. The radiation irradiation device according to claim 6, wherein the movable part is a plate-shaped member or a tubular member that slides in the extension direction of the arm part.

13. The radiation irradiation device according to claim 7, wherein the movable part is a plate-shaped member or a tubular member that slides in the extension direction of the arm part.

14. The radiation irradiation device according to claim 4, wherein the arm locking part restricts the rotational movement of the arm part, using a locking pin, and a locking part to which the locking pin is locked, and
wherein the arm unlocking part releases the locking performed by the locking part as the locking pin is moved by the movement of the movable part.

15. The radiation irradiation device according to claim 1, wherein the arm part moves rotationally only around one axis.

16. The radiation irradiation device according to claim 1, wherein the support member is configured to be rotatable with an axis passing through a center of a connecting portion of the support member to the body part and extending in a vertical direction as a rotational axis.

17. The radiation irradiation device according to claim 16, further comprising:
a support member locking part that restricts the rotation of the support member.

18. The radiation irradiation device according to claim 17, wherein the support member locking part restricts the rotation in a case where the support member is located at a center of a rotational angle.

19. The radiation irradiation device according to claim 17, wherein the support member locking part restricts the rotation of the support member only in a case where the rotational movement of the arm part is restricted using the arm locking part.

20. The radiation irradiation device according to claim 17, wherein the support member locking part releases the restriction of the rotation of the support member in an interlocking manner with the rotational movement of the arm part.

21. The radiation irradiation device according to claim 1, wherein the support member is configured to be rotatable with respect to the body part.

* * * * *